United States Patent
Clayton

(10) Patent No.: US 12,317,406 B2
(45) Date of Patent: May 27, 2025

(54) ACCELERATOR AND PARTICLE BEAM TRANSPORT SYSTEMS AND METHODS

(71) Applicant: Varian Medical Systems, Inc., Palo Alto, CA (US)

(72) Inventor: James E Clayton, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 215 days.

(21) Appl. No.: 17/709,217

(22) Filed: Mar. 30, 2022

(65) Prior Publication Data

US 2023/0319973 A1    Oct. 5, 2023

(51) Int. Cl.
| | |
|---|---|
| H05H 9/02 | (2006.01) |
| H05H 7/00 | (2006.01) |
| H05H 7/04 | (2006.01) |
| H05H 7/08 | (2006.01) |

(52) U.S. Cl.
CPC .............. *H05H 9/02* (2013.01); *H05H 7/001* (2013.01); *H05H 7/04* (2013.01); *H05H 7/08* (2013.01); *H05H 2007/045* (2013.01); *H05H 2007/084* (2013.01)

(58) Field of Classification Search
None
See application file for complete search history.

(56) References Cited

U.S. PATENT DOCUMENTS

| | | | |
|---|---|---|---|
| 4,726,046 A | 2/1988 | Nunan | |
| 8,198,587 B2 * | 6/2012 | Whittum | G21K 1/093 250/311 |
| 8,385,505 B2 * | 2/2013 | Coon | H01J 35/103 378/127 |
| 8,405,044 B2 * | 3/2013 | MacKinnon | A61N 5/1081 315/501 |
| 8,541,756 B1 * | 9/2013 | Treas | G01N 23/10 250/398 |

(Continued)

FOREIGN PATENT DOCUMENTS

WO    WO-2021/208067 A1    10/2021

OTHER PUBLICATIONS

B. Andreassen et al. 'Development of an efficient scanning and purging magnet system for IMRT with narrow high energy photon beams', *Nuclear Instruments and Methods in Physics Research* A 612 (2009), pp. 201-208.

(Continued)

*Primary Examiner* — Srinivas Sathiraju
(74) *Attorney, Agent, or Firm* — Harness, Dickey & Pierce, P.L.C.

(57) ABSTRACT

Presented systems and methods enable efficient and effective radiation planning and treatment, including accurate and convenient transmission of the radiation towards a tissue target. In one embodiment, a radiation system includes an electron gun, a bend magnet, a scan control component, and an electron beam entry angle control component. The electron gun is configured to generate electrons. The linear accelerator is configured to accelerate the electrons in an electron beam. The bend magnet is configured to bend the path of the electron beam. The scan control component controls movement of the electron beam in a scan pattern. The electron beam entry angle control component is configured to control the entry angle of the electron beam.

23 Claims, 13 Drawing Sheets

(56) References Cited

U.S. PATENT DOCUMENTS

| | | | |
|---|---|---|---|
| 10,252,083 B2* | 4/2019 | Clayton | A61N 5/1067 |
| 10,485,993 B2* | 11/2019 | Goer | A61N 5/1049 |
| 10,622,114 B2* | 4/2020 | Purwar | G21K 1/093 |
| 10,661,102 B2* | 5/2020 | Clayton | A61N 5/1083 |
| 10,843,011 B2* | 11/2020 | Trail | H01J 37/073 |
| 10,912,952 B2* | 2/2021 | Clayton | A61N 5/1067 |
| 10,940,333 B2* | 3/2021 | Thieme | A61N 5/1049 |
| 11,285,341 B2* | 3/2022 | Goer | A61N 5/1067 |
| 11,547,873 B2* | 1/2023 | Clayton | A61N 5/1067 |
| 11,712,585 B2* | 8/2023 | Clayton | A61N 5/1067 378/65 |
| 2004/0079899 A1 | 4/2004 | Ma | |
| 2013/0015364 A1* | 1/2013 | MacKinnon | H05H 7/001 250/396 ML |
| 2013/0144104 A1* | 6/2013 | Adler, Jr. | G21F 5/02 600/1 |
| 2013/0188856 A1* | 7/2013 | Adler, Jr. | A61B 6/463 382/132 |
| 2014/0171725 A1* | 6/2014 | Adler | G21F 3/00 600/1 |
| 2014/0294147 A1* | 10/2014 | Chen | G01V 5/232 378/57 |
| 2015/0352376 A1* | 12/2015 | Wiggers | A61B 6/586 378/207 |
| 2017/0080253 A1* | 3/2017 | Clayton | A61N 5/1067 |
| 2017/0225015 A1* | 8/2017 | Thieme | A61B 6/4258 |
| 2017/0296844 A1* | 10/2017 | Trail | H01J 1/46 |
| 2018/0028143 A1* | 2/2018 | Wiggers | A61B 6/588 |
| 2018/0272155 A1* | 9/2018 | Thieme | A61B 6/4258 |
| 2018/0277276 A1* | 9/2018 | Purwar | G21K 5/04 |
| 2018/0280734 A1* | 10/2018 | Clayton | A61N 5/1083 |
| 2019/0054318 A1* | 2/2019 | Goer | A61N 5/1067 |
| 2019/0175946 A1* | 6/2019 | Clayton | A61N 5/1067 |
| 2020/0086144 A1* | 3/2020 | Goer | A61N 5/1067 |
| 2020/0227184 A1* | 7/2020 | Purwar | A61N 5/1043 |
| 2020/0306562 A1* | 10/2020 | Godeke | A61N 5/1081 |
| 2021/0077831 A1* | 3/2021 | Clayton | A61N 5/1067 |
| 2021/0085999 A1 | 3/2021 | Bartkoski et al. | |
| 2021/0138272 A1* | 5/2021 | Thieme | A61N 5/1075 |
| 2021/0282735 A1* | 9/2021 | Wiggers | A61B 6/586 |
| 2023/0069176 A1* | 3/2023 | Clayton | A61N 5/1067 |
| 2023/0090348 A1* | 3/2023 | Poehlmann-Martins | A61N 5/1042 600/1 |
| 2023/0319973 A1* | 10/2023 | Clayton | H05H 7/001 315/50 |

OTHER PUBLICATIONS

B. Andreassen 'Development of improved radiation therapy techniques using narrow scanned photon beams' *Department of Physics*, Stockholm University, Sweden by Universitets service IS-AB, 2010, pp. 1-36.

\* cited by examiner

Raster Scan

Spot Scanning Pencil Beam

Pencil Beam

700

---

710

Generating a particle beam.

---

720

Directing the particle beam in a scan pattern.

---

730

Controlling the spread of the particle beam.

---

740

Forwarding the particle beam towards a target tissue.

Fig. 7

ACCELERATOR AND PARTICLE BEAM TRANSPORT SYSTEMS AND METHODS

BACKGROUND

Radiation therapy is utilized in various medical treatments. Radiation beams can be utilized in a number of different applications and accurately applying an appropriate amount of radiation can be very important. Radiation therapy usually involves directing a beam of high energy proton, photon, ion, or electron radiation ("therapeutic radiation") into a tissue target or tissue target volume (e.g., a tissue volume that includes a tumor, lesion, etc.). The radiation beams are typically used to stop the growth or spread of the targeted tissue cells by killing them or degrading their cell division ability. While radiation therapy is generally considered beneficial, there can be a number of potential side effects. The side effects can include unintended damage to DNA of healthy tissue cells. The effectiveness of radiation therapy is primarily a function of the dose or amount of ionizing radiation that is applied to an intended tissue target (e.g., tumor, cancerous cells, etc.) while avoiding impacts to healthy cells.

Various treatment approaches have characteristics that can offer significant benefits. It was recently discovered that delivering a therapeutic dose at ultra-high dose rates (e.g., >40 Gy/s, etc.), referred to as FLASH dose rate delivery, reduces the radiation sensitivity of healthy tissue, but not of tumors. Delivering the same dose, but at ultra-high dose rates can increase the therapeutic ratio over conventional treatment delivery. Proton and electron radiation approaches can generally provide higher dose rates.

While the potential benefits of using electron beam radiation can be significant, the realization of this objective has traditionally been very challenging in practice (e.g., not practical, not possible, etc.). There are several significant potential detrimental side effects associated with utilizing electron beam radiation in medical procedures. For example, electron beam energy levels and path configurations can be problematic. FIG. 1A is a block diagram showing diverging electron beams generally have different lengths. The electron paths L1 and L3 are longer than L2. In one example, the length or distance L to a tumor is approximately 40-60 cm and the width t of the tumor is approximately 0-30 cm, giving a total (L+t) measurement of approximately 40-90 cm. The difference in electron paths makes accurate and uniform dose delivery difficult and less efficient. Furthermore, in general it is desirable to keep electron beam energy levels low so as to prevent excessive radiation doses to organs at risk or other critical structures, however too much energy can be applied to the skin above a target tissue if the electron beam energy levels are too low.

SUMMARY

Presented systems and methods enable efficient and effective radiation planning and treatment, including accurate and convenient transmission of the radiation towards a tissue target. In one embodiment, a radiation system includes an electron gun, a bend magnet, a scan control component, and an electron beam entry angle control component.

The electron gun is configured to generate electrons. The linear accelerator is configured to accelerate the electrons in an electron beam. The bend magnet is configured to bend the path of the electron beam. The scan control component controls movement of the electron beam in a scan pattern. The electron beam entry angle control component is configured to control the entry angle of the electron beam. In one exemplary implementation, the electron beam entry angle control component is configured to control the entry angle of the electron beam at varying distances from the electron beam entry angle control component.

It is appreciated the electron beam entry angle control component can change the beam configuration in various ways. In one embodiment, the electron beam entry angle control component includes a normal incident control component configured to receive a plurality of electron beams with electrons traveling in diverging directions and redirect the electrons into a normal incidence direction. In one embodiment, the electron beam entry angle control component includes a convergent control component configured to receive a plurality of electron beams with electrons traveling in a diverging direction and redirect the electrons into a convergent direction. The electron beam entry angle control can be directed to controlling aspects of radiation impacts on a patient due to penetration of the electron beam. The electron beam entry angle control can be directed to control the penetration characteristics of a plurality of electron beams into a patient, including controlling radiation dose delivery to a tissue target. In one exemplary implementation, the electron beam entry angle control is directed to controlling the penetration characteristics of an electron beam into a patient, including avoidance of detrimental radiation impacts on non-target areas within a patient. The electron beam entry angle control component can include electromagnets configured to create a magnetic field that changes divergent paths of the electrons in the electron beam to substantially parallel paths. The electron beam entry angle control component can include multipole magnets configured to create a magnetic field that changes divergent paths of the electrons in the electron beam to convergent paths. The electron beam entry angle control component can include sector magnets configured to create a magnetic field that changes divergent paths of the electrons in the electron beam to paths with a different divergence.

In one embodiment, a method comprises generating a particle beam, directing the particle beam in a scan pattern, controlling the entry angle distribution of the particle beam, and forwarding the particle beam towards a target tissue. The particle beam can be an electron beam, a proton beam, and so on. Controlling the entry angle distribution of the particle beam can include directing the particles in the particle beam into parallel paths. Controlling the entry angle distribution of the particle beam can include directing the particles in the particle beam into convergent paths. In one exemplary implementation, the entry angle of the particle beam is altered based upon a dose delivery characteristic. The entry angle of the particle beam can be altered based upon a depth penetration characteristic.

In one embodiment, a system includes a particle beam generation component configured to generate a particle beam, a scan control component that controls movement of the particle beam in a scan pattern, and a particle beam entry angle control component that controls the entry angle of the particle beam. In one exemplary implementation, controlling the entry angle of the particle beam includes controlling the size of a cross-section area of the particle beam at varying distances from the electron beam entry angle control component. The particle beam entry angle control component can be configured to receive a beam with particles traveling in a first diverging direction and redirect the particles into a second diverging direction. The particle beam entry angle control component can be configured to receive a beam with particles traveling in a diverging direction and redirect the particles into a substantially parallel and normal incidence direction. The particle beam entry angle control component can be configured to receive a particle beam with electrons traveling in a diverging direction and redirect the particles into a convergent direction. In one exemplary implementation, the particle beam entry angle control is directed to controlling the penetration characteristics of the particle beam into a patient, including radiation dose delivery to the tissue target. The particle beam entry angle control can be directed to controlling the penetration characteristics of the particle beam into a patient, including avoidance of detrimental radiation impacts on non-target areas within the patient. In one embodiment, the non-target areas include heathy tissue, structures or organs proximate a tissue target, and so on.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure. The drawings are not intended to limit the present invention to the particular implementations illustrated therein. The drawings are not to scale unless otherwise specifically indicated.

FIG. 7 is a block diagram of an exemplary method in accordance with one embodiment.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Presented systems and methods enable efficient and effective radiation planning and treatment, including accurate and convenient transmission of the radiation towards a tissue target. In one embodiment, the use of large momentum acceptance particle beam transport beamlines coupled with a particle beam scanning system that uses convergent, divergent, or normal incidence beam paths to a tissue target (e.g., tumor, etc.) facilitates flexible changes in the dose distribution. Scanning and adjusting a distribution spread of particle beams in accordance with the described systems and methods can yield dose distributions that have superior conformity to the tissue target (e.g., tumor site, etc.). The resulting particle beam lines can deliver more precise dose plans than those of traditional approaches (e.g., utilizing scattering foils, etc.). The implementation of the particle beam distribution or entry angle adjustment control (e.g., converging, normally incident, diverging, etc.) can provide degrees of freedom that are not typically available in conventional systems. The addition of variations in beam intensity while scanning on a pulse-by-pulse basis also adds a degree of freedom that is not used in current treatment modalities. In one embodiment, a entry angle control system can enable greater degrees of freedom and particle beam energy variation than a traditional system that is limited to less than 3%, which does not allow for much in the way of beam energy variation.

Figure 1A:
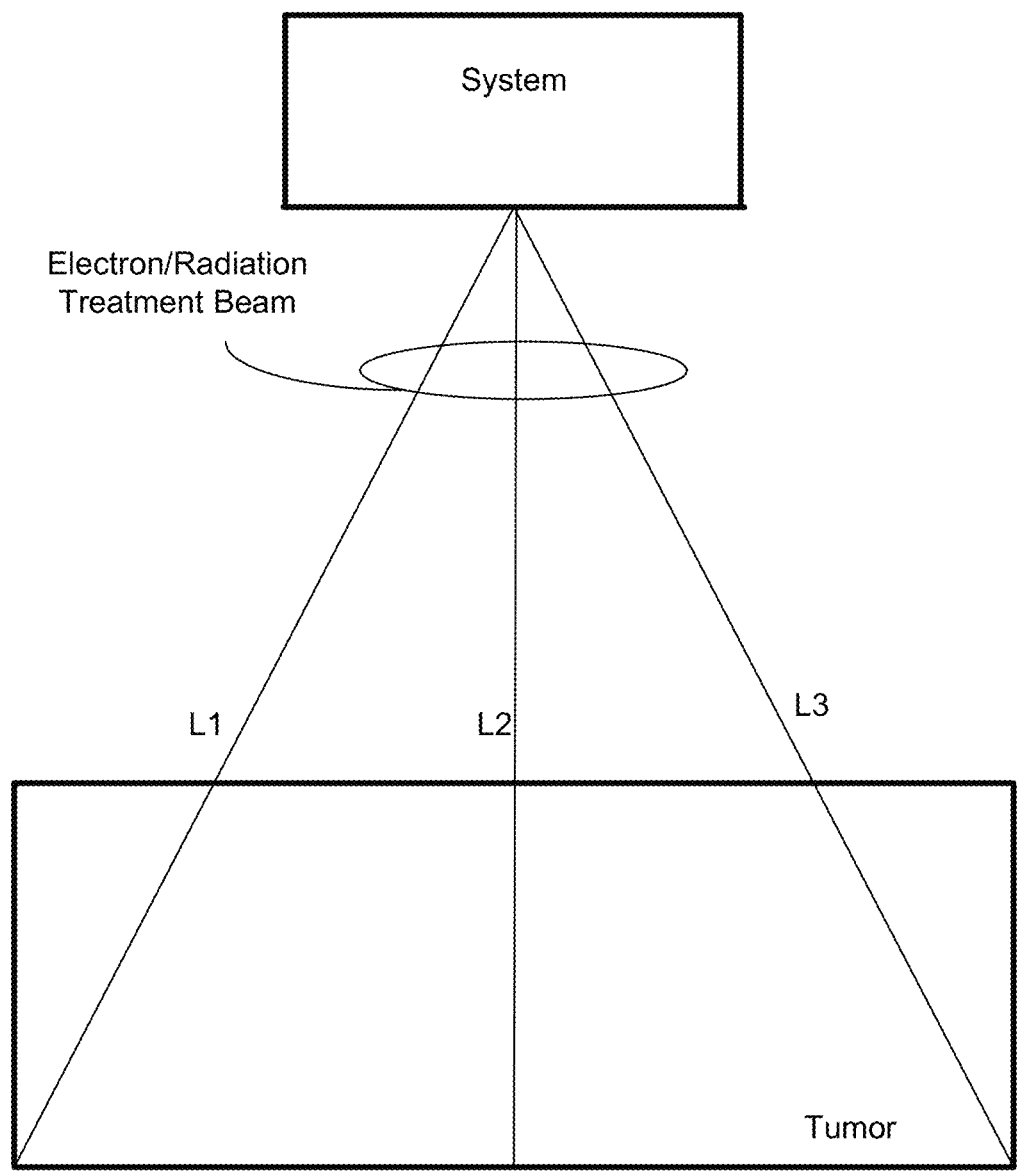
FIG. 1A is a block diagram of an exemplary traditional divergent electron beam path.
Figure 1B:
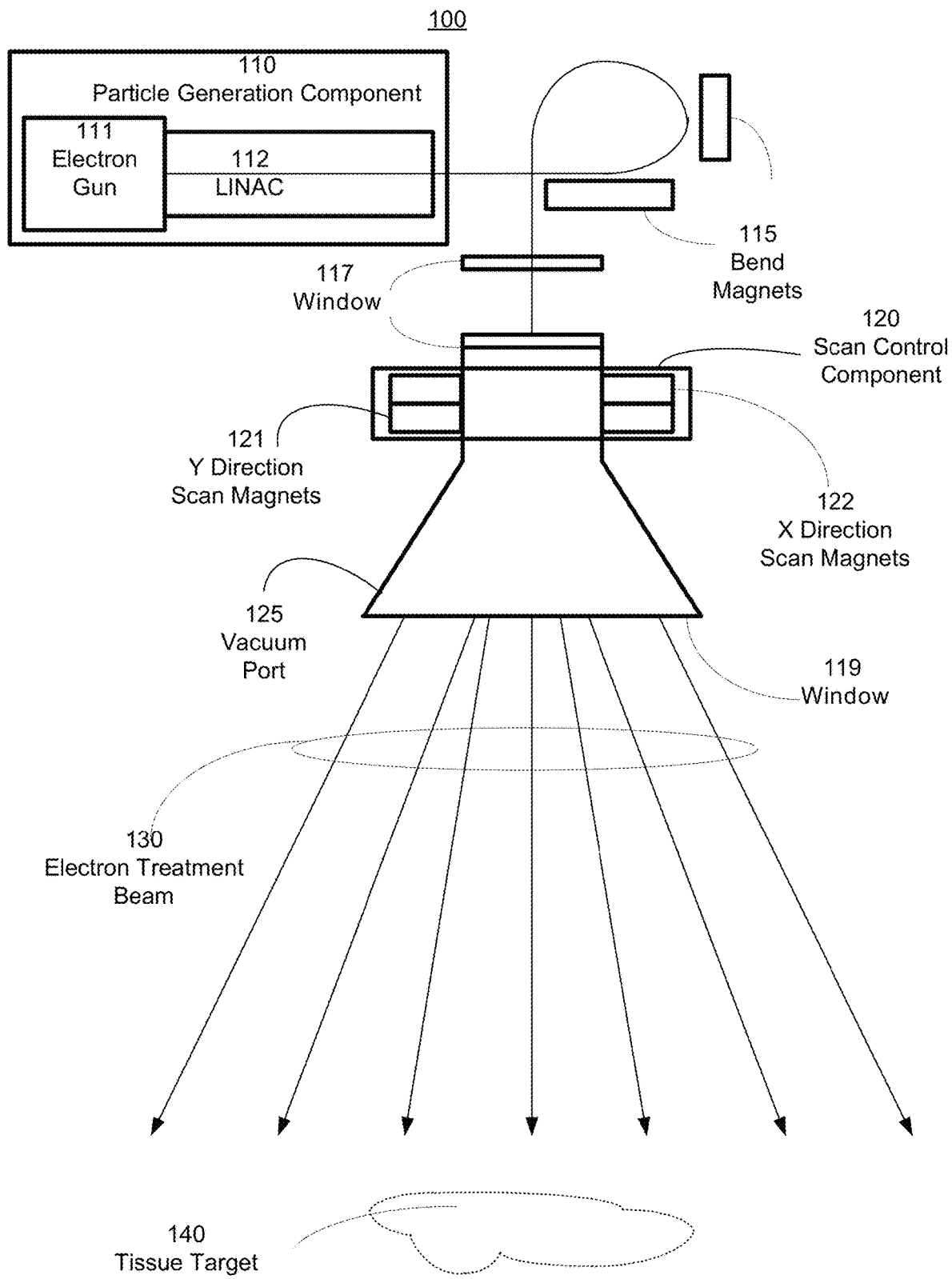
FIG. 1B is a block diagram of an exemplary radiation system in accordance with one embodiment.

FIG. 1B is a block diagram of an exemplary traditional system 100. System 100 includes particle generation component 110, bend magnets 115, windows 117 and 119, scan control component 120, Y-direction scan magnets 121, X-direction scan magnets 122, and vacuum port 125. It is appreciated the windows can be made from or include various materials (e.g., Beryllium (Be), Titanium (Ti), Kapton, etc.). In one embodiment, particle generation component 110 includes electron gun 111 and Linear Accelerator (LINAC) 112, The particle generation component 110 generates electrons that are accelerated by LINAC 111 in an electron beam towards the bend magnets 115. The bend magnets 115 bend the electron beam directing the electron beam though the windows 117 into the path of the scan control component 120 which directs the electron beam in a scan pattern. In one embodiment, scan control component 120 includes Y-direction scan magnets 121 and X-direction scan magnets 122. As illustrated in FIG. 1B the electron treatment beams diverge as they leave the scan or vacuum port 125. The electron treatment beam 130 flows from the scan magnets though the scan or vacuum port 125 and exits the system through the window 119. Some of the electron treatment beam 130 travels towards the tissue target 140 and some diverges away from the tissue target 140. In addition, some of the electrons travel difference distances before impacting tissue target 140. The dose may not be uniform due to the different path lengths. Furthermore, dose efficiency and accuracy may be limited since adjustability of the dose depth distribution is substantially set by the divergence of the electrons, other things (e.g., beam energy, etc.) being equal.

Figure 2A:
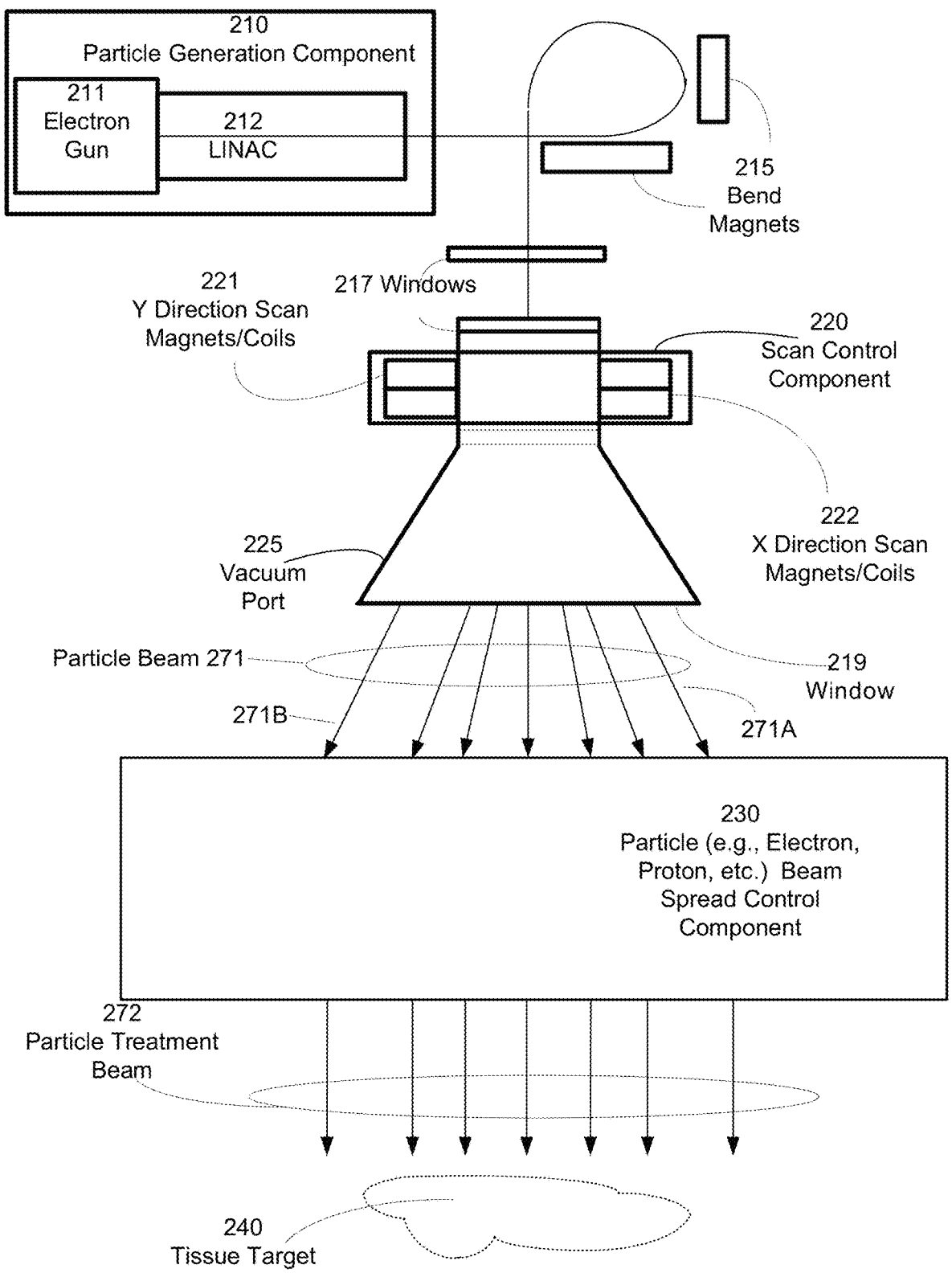
FIG. 2A is a block diagram of an exemplary system in accordance with one embodiment.

FIG. 2A is a block diagram of an exemplary system 200A in accordance with one embodiment. System 200A includes particle beam generation component 210, bend magnets 215, windows 217 and 219, scan control component 220, scan or vacuum port 225, and particle beam entry angle control component 230. Particle beam generation component 210 generates a particle beam. The bend magnets 215 bend the particle beam directing the particle beam though the windows 217 into the path of the scan control component 220, which directs the particle beam in a scan pattern. The scan control component 220 can include magnetic scan coils. In one embodiment, scan control component 220 includes Y-direction scan magnets 221 and X-direction scan magnets 222. The particle beam flows from the scan magnets though the scan or vacuum port 225 and window 219 towards the particle beam entry angle control component 230. If is appreciated the windows can be made from or include various materials (e.g., Beryllium (Be), Titanium (Ti), Kapton, etc.). Pulsing of LINAC 212 and operation of the scan magnets 221,222 produce a time series of particle beams 271. For example, at a first time, particle beam 271A emerges from window 219, and at a second time, particle beam 271B emerges from window 219. The particle beam entry angle control component 230 adjusts the paths of the particles (e.g., electron paths, proton paths, etc.) in particle beam 271, resulting in an adjusted distribution/entry angle of the particle treatment beam 272. In one exemplary implementation, the particle treatment beam 272 is an electron treatment beam.

In one embodiment, the particles of the particle beam 271 are diverging when they leave the scan or vacuum port 225 (e.g., exit the through the window 219) and as they enter the particle beam entry angle control component 230. The particle beam entry angle control component 230 can alter the paths of the particles so that the particles are traveling in substantially parallel paths. As illustrated in FIG. 2A, the particle paths in the particle treatment beam 272 are basically parallel as they leave the particle beam entry angle control component 230 traveling towards the tissue target 240. In one exemplary implementation, the particle paths in the particle treatment beam 272 have a normal incidence with respect to the exit plane of the particle beam entry angle control component 230. Particle treatment beam 272 is directed towards tissue target 240.

It is appreciated the present entry angle control approaches are applicable to various types of particle beams (e.g., electron beams, proton beams, etc.). For ease of explanation, most of the description herein is directed to electron beams. Similar systems and methods can be directed to other particle beams (e.g., proton beams, etc.). In one embodiment, particle beam generation component 210 includes electron gun 211 and LINAC 212. The particle beam generation component 210 generates electrons that are accelerated by LINAC 212 in an electron beam towards the bend magnets 215. In one embodiment, LINAC 212 outputs electrons beams in the 2-25 MeV range. In one exemplary implementation the system can include an energy selector and slits.

Figure 2B:
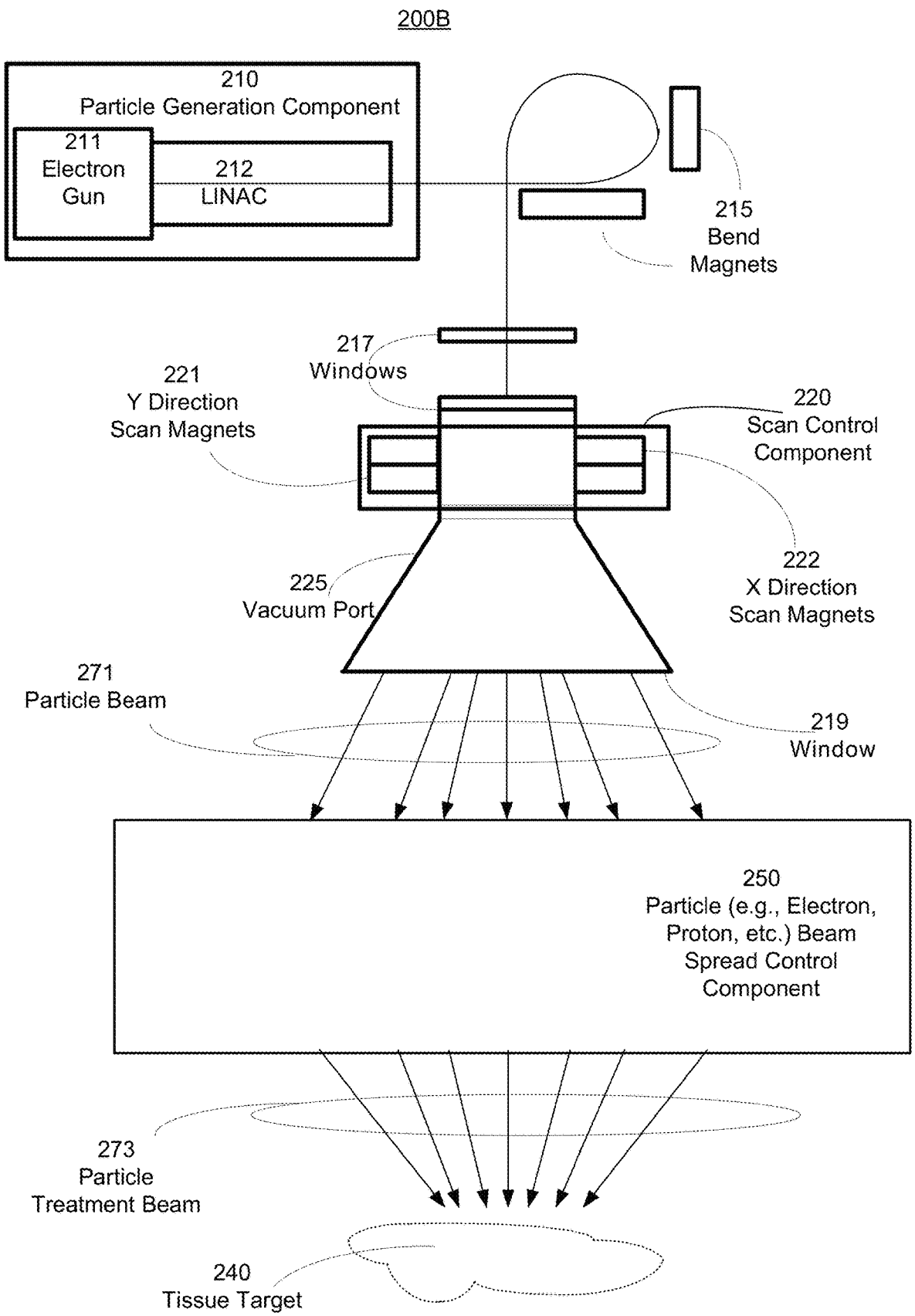
FIG. 2B is a block diagram of an exemplary system in accordance with one embodiment.

FIG. 2B is a block diagram of an exemplary system 200B in accordance with one embodiment. System 200B is similar to system 200A except particle beam entry angle control component 250 alters the entry angle of a particle beam from diverging to converging (instead of normal incidence or parallel as in system 200A). The particle beam entry angle control component 250 adjusts the particle paths and resulting entry angles of the particle treatment beam 273. In one embodiment, the particles of the particle beam 271 are diverging when they leave the scan or vacuum port 225 (e.g., exit the through the window 219) and as they enter the particle beam entry angle control component 250. The particle beam entry angle control component 250 alters the paths of the particles so that the particles are traveling in substantially converging paths. As illustrated in FIG. 2B the particle paths in the particle treatment beam 273 are converging as they leave the particle beam entry angle control component 250 and travel towards the tissue target 240.

In one embodiment, a particle beam entry angle control component is not limited to a particular type of entry angle adjustment and the particle beam entry angle control components can adjust distribution/entry angle of the output particle treatment beam in various configurations. (e.g., parallel beam, convergent beam, etc.). It is appreciated a particle beam entry angle control component can have various configurations and features. In one embodiment, a particle beam entry angle control component and other components in a system can be temperature controlled (e.g., air cooled, water cooled, etc.). In one exemplary implementation, the interior of a particle beam entry angle control component and other components in a system can form a vacuum.

Figure 3:
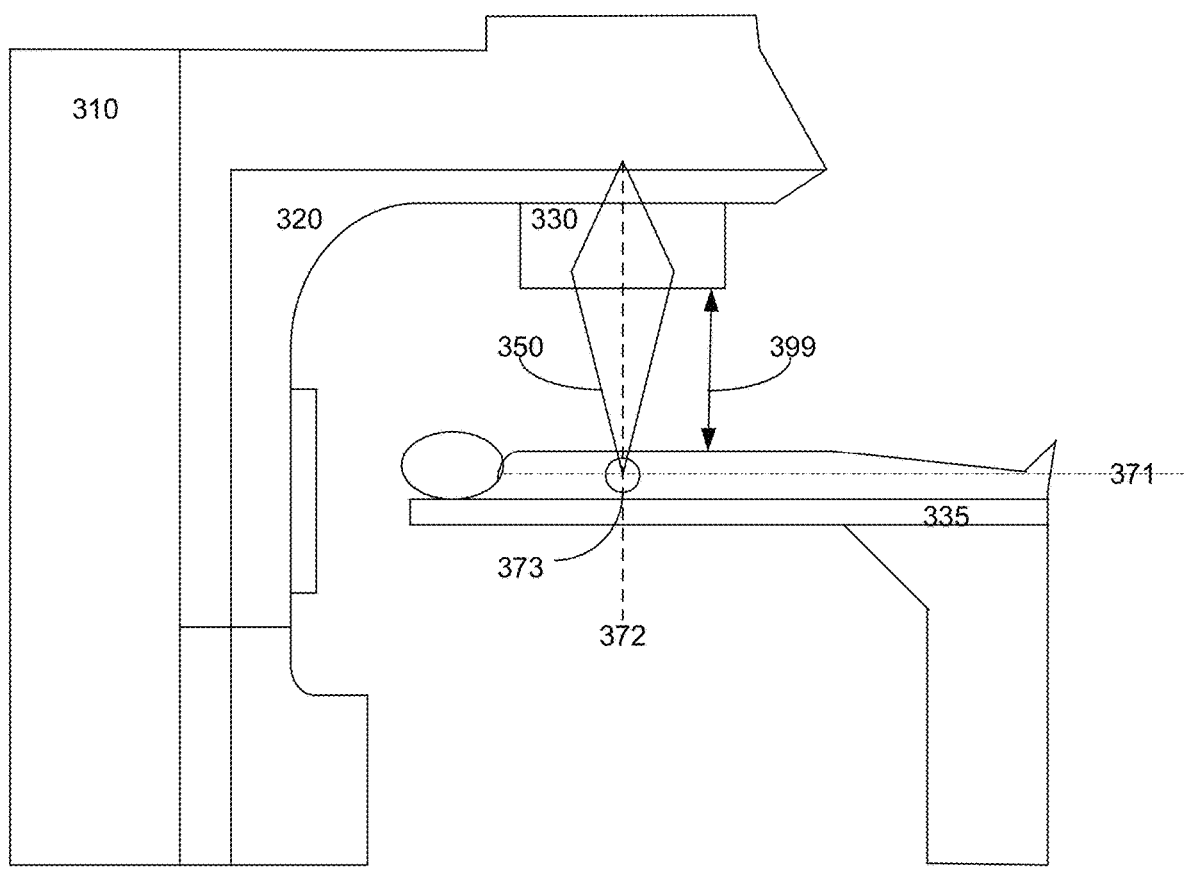
FIG. 3 illustrates a block diagram of an exemplary radiation treatment system in accordance with one embodiment.

FIG. 3 illustrates a block diagram of an exemplary radiation treatment system 300 in accordance with one embodiment. Radiation treatment system 300 may be similar to a Varian TrueBeam® radiotherapy system, commercially available from Varian Medical Systems, Palo Alto, CA.

Stand 310 supports a rotatable gantry 320 with a treatment head 330. The treatment head 330 may extend into the gantry 320. In proximity to stand 310 there is arranged a control unit (not shown) which includes control circuitry for controlling the different modes of operation of the system 300. In one embodiment, treatment head 330 includes a particle beam entry angle control component (e.g., similar to particle beam entry angle control component 230, etc.).

Radiation treatment system 300 comprises a radiation system (e.g., similar to 200A and 200B in FIGS. 2A and 2B, etc.), for example, within gantry 320, utilized to create a radiation beam. Typically, radiation treatment system 300 is capable of generating either a particle (e.g., electron, proton, etc.) beam or an X-ray (photon) beam for use in the radiotherapy treatment of patients on a treatment couch 335. In one embodiment, a high voltage source is provided within the stand and/or in the gantry to supply voltage to an electron gun (not shown) positioned on an accelerator guide located in the gantry 320. Electrons are emitted from the electron gun into an accelerator where they are accelerated. A source supplies radio frequency (microwave) power for the generation of an electric field within a waveguide. The electrons emitted from the electron gun are accelerated in the waveguide by the electric field, and exit the waveguide as a high-energy electron beam for example, at megavoltage energies. In one embodiment, the gantry includes a component (e.g., bend magnets, etc.) for redirecting the beams (e.g., in the direction of a patient, etc.).

As illustrated in FIG. 3, a patient is shown lying on the treatment couch 335. The radiation treatment beam 350 is emitted from the treatment head 330 (e.g., as described above, etc.) towards the patient. In one exemplary implementation, a patient plane 371 is usually positioned through the tissue target and about one meter from treatment head 330, and the rotational axis of the gantry 320 is located on the plane 371, such that the distance between the target and the isocenter 373 remains substantially constant when the gantry 320 is rotated. It is appreciated that for electron FLASH therapy, the patient plane 371 may be less than one meter from the particle source in treatment head 330. The isocenter 373 may be at the intersection between the patient plane 371 and the central axis 372 of radiation beam 350. A treatment volume to be irradiated may be located about the isocenter 373. It is appreciated that some treatment plans may utilize a primary target that is off of the central beam axis, and such arrangements are within the scope of embodiments in accordance with the present invention.

It is appreciated that various particle beam entry angle control component configurations can be implemented. A particle beam entry angle control component can include various types of magnets (e.g., sector magnets, electro magnets, multipole magnets, etc.) that can create various outputs, including diverging, normal incidence, and converging beam entry angle. In one embodiment, an electro magnet is utilized to create diverging, normal incidence, and converging beam entry angles.

Figure 4A:
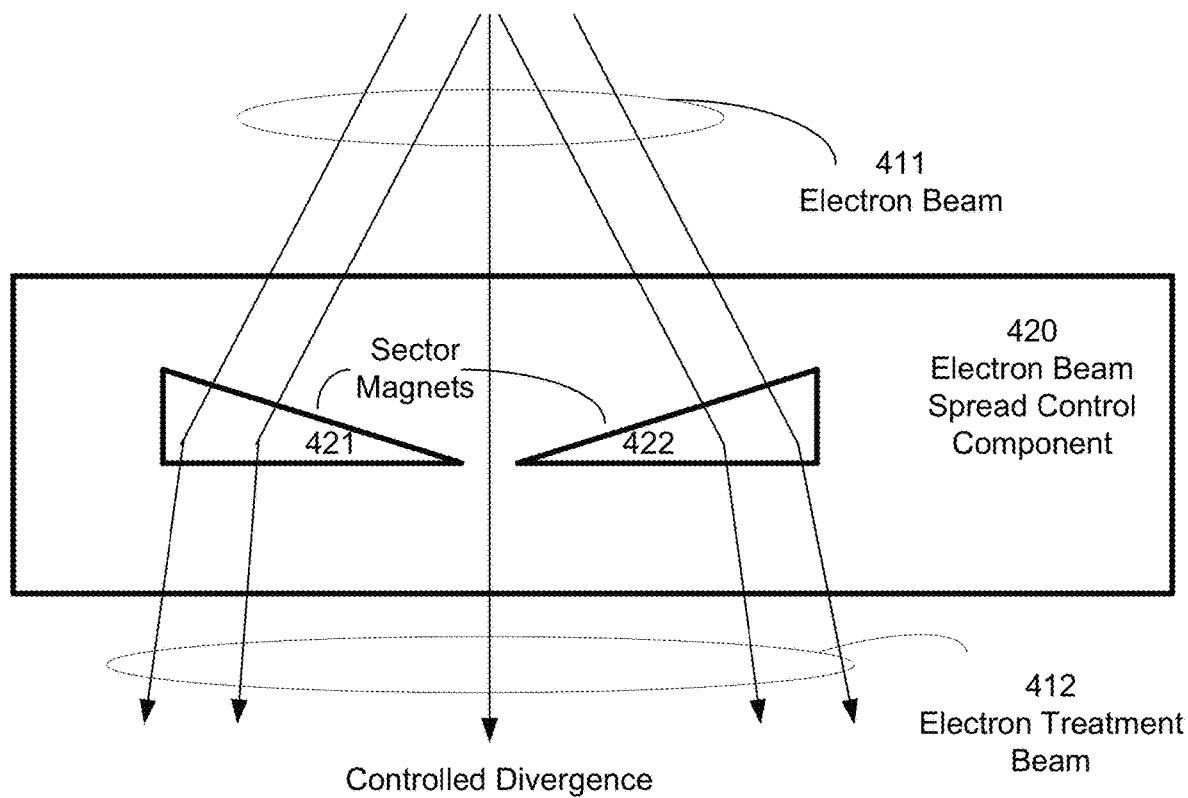
FIG. 4A is a block diagram of an exemplary electron beam entry angle control component in accordance with one embodiment.

FIG. 4A is a block diagram of an exemplary electron beam entry angle control component in accordance with one embodiment. The divergence of electron paths in electron treatment beam 412 is controlled. Electron beam entry angle control component 420 includes sector magnets 421 and 422. The sector magnets 421 and 422 apply a magnetic field to the electrons in the electron beam 411. The magnetic field can alter the paths of diverging electrons in electron beam 411 to diverge differently (e.g., lesser divergence, more divergence, etc.) to one another in the electron treatment beam 412. In one embodiment, the electrons in the electron treatment beam are in paths that are divergent at the exit surface of the electron beam entry angle control component 420. In one exemplary implementation, the electrons in the electron treatment beam 412 also enter a target tissue in a divergent orientation. While both electron beam 411 and electron treatment beam 412 are diverging, the amount of divergence in the electron treatment beam 412 is controlled to an appropriate/desired amount. In one exemplary implementation, a divergent particle treatment beam with a controlled amount of divergence is desirable to reach a dose distribution at a desired depth (e.g., shallow, etc.). In one embodiment, electron beam entry angle control component 420 includes a divergent control component configured to receive a beam with particles traveling in a first diverging direction and redirect the particles into a second diverging direction.

Figure 4B:
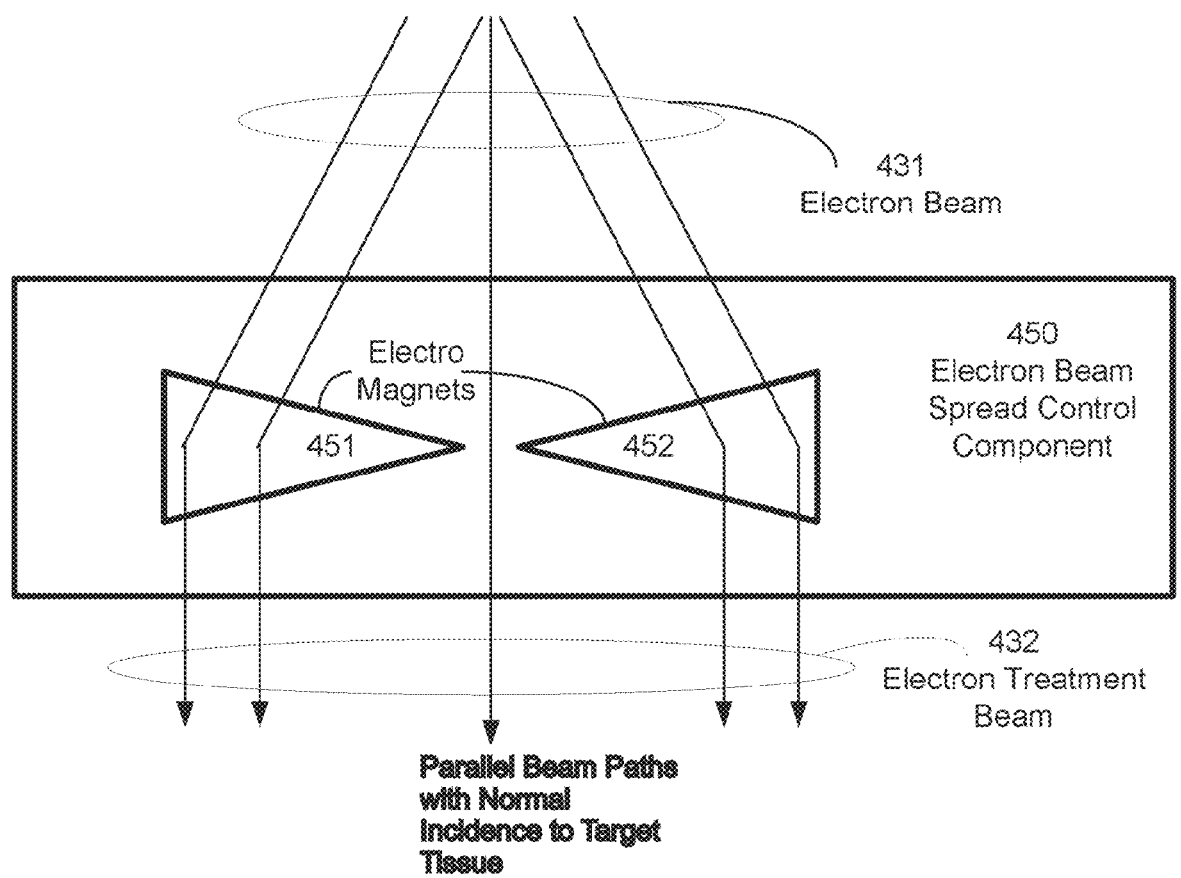
FIG. 4B is a block diagram of another exemplary electron beam entry angle control component in accordance with one embodiment.

FIG. 4B is a block diagram of an exemplary electron beam entry angle control component in accordance with one embodiment. Electron paths in electron treatment beam 432 are substantially parallel. Electron beam entry angle control component 450 includes electro magnets 451 and 452. The electro magnets 451 and 452 apply a magnetic field to the electrons in the electron beam 431. The magnetic field can alter the paths of diverging electrons in electron beam 431 to be essentially parallel to one another in the electron treatment beam 432. In one embodiment, the electrons in the electron treatment beam 432 are in paths that have a normal incidence (e.g., substantially perpendicular, etc.) to the exit surface of the electron beam entry angle control component 450. In one exemplary implementation, the electrons in the electron treatment beam 432 also enter a target tissue in a normal/perpendicular orientation to the target tissue, with the paths of the electrons in the electron treatment beam 432 being essentially parallel to one another. In one embodiment, electron beam entry angle control component 450 includes a normal incident control component configured to receive a beam with particles traveling in diverging paths and redirect the particles into substantially parallel paths having a normal incident direction to the exit surface of the electron beam entry angle component 450.

Figure 4C:
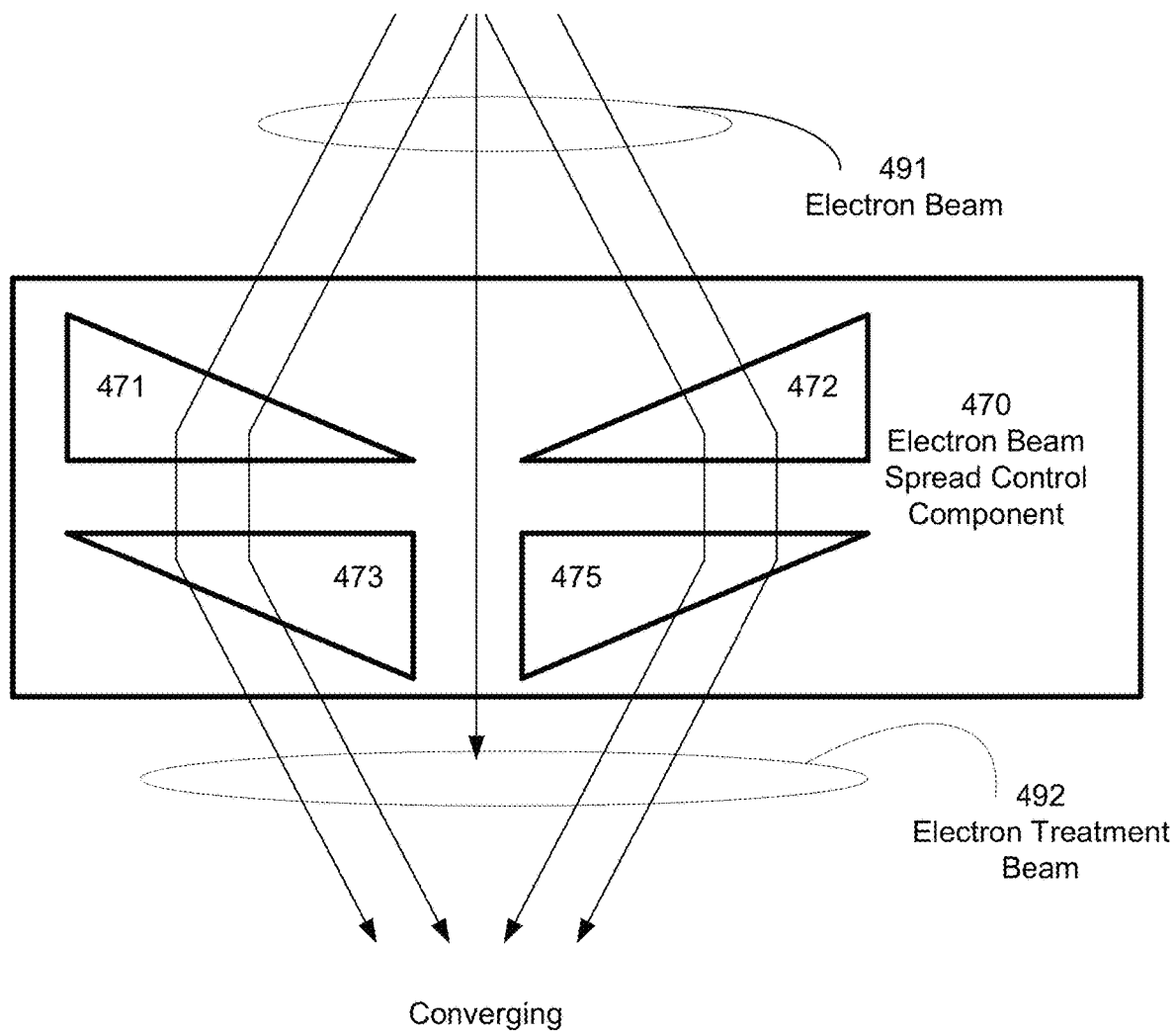
FIG. 4C is a block diagram of another exemplary electron beam entry angle control component in accordance with one embodiment.

FIG. 4C is a block diagram of another exemplary electron beam entry angle control component in accordance with one embodiment. Electron paths in electron treatment beam 492 converge. Electron beam entry angle control component 470 includes multipole magnets 471, 472, 473, and 475. The multipole magnets apply a magnetic field to the electrons in the electron beam 491. The magnetic field can alter the paths of diverging electrons in electron beam 491. Multipole magnets 471 and 472 cause the electron paths to be substantially parallel to one another and multipole magnets 473 and 474 cause the electron paths to converge. In one embodiment, electron beam entry angle control component 470 can include a quadrupole magnet. In one embodiment, the electrons in the electron treatment beam 492 are in paths that are converging when they exit the electron beam entry angle control component 450. In one exemplary implementation, the electrons in the electron treatment beam 492 also enter a target tissue in a converging orientation. In one embodiment, electron beam entry angle control component 470 includes a convergent control component configured to receive a particle beam with electrons traveling in a diverging direction and redirect the particles into a convergent direction.

In one exemplary implementation, a convergent particle beam has a deeper dose distribution at a given energy than a normally incident particle beam, and a divergent particle beam has a shallower dose distribution at a given energy than a normally incident particle beam. In one embodiment, a particle beam normally incident to the skin has a dose depth defined as D_0. A convergent or divergent particle bream has a dose depth that is 5-10% deeper or shallower respectively, depending on the particle beam energy and amount of convergence or divergence. The distribution or entry angle adjustment in conjunction with a particle beam line that has a larger momentum acceptance can add degrees for freedom to improve the dose distributions in tissue targets.

Figure 5:
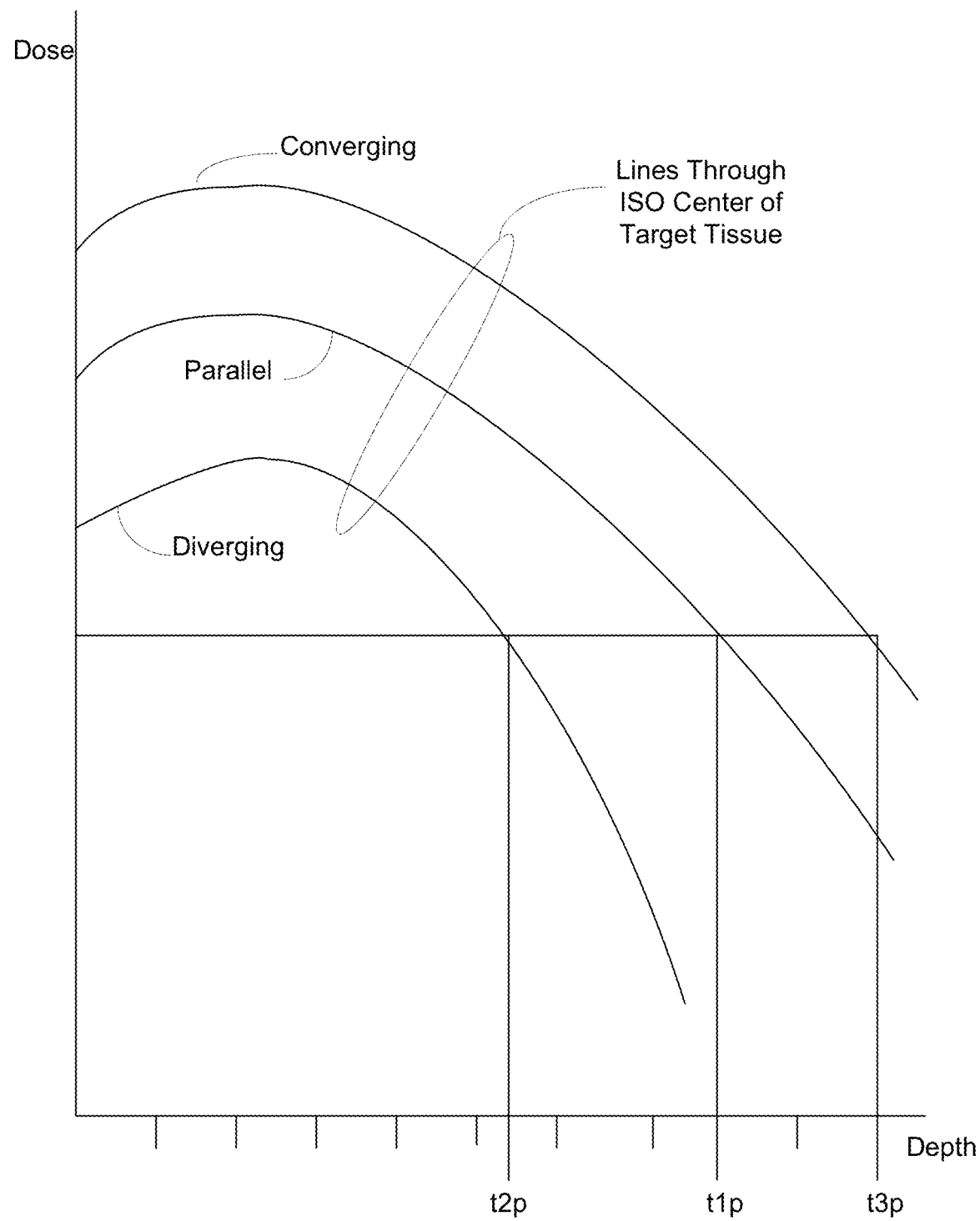
FIG. 5 is an illustration of an exemplary dose distribution graph in accordance with one embodiment.

FIG. 5 is an illustration of an exemplary dose distribution graph in accordance with one embodiment. The dose amount is shown on the Y-axis and the thickness times the density of the material is shown on the X-axis. The t2p depth corresponds to an electron beam with electron beam entry angle adjustment and the resulting diverging electron paths. In one implementation, the beam is not entering normal to the patient. The t1p depth corresponds to an electron beam with an electron beam entry angle adjustment and resulting corresponding parallel electron paths. The t3p depth corresponds to an electron beam with further electron beam entry angle adjustment and resulting converging electron paths. In one embodiment, the energy is 5-25 MeV producing a dose of 0.9 to 12 Gy/cm$^3$ with a dose rate of 40 to 100 Gy/s.

Figure 6:
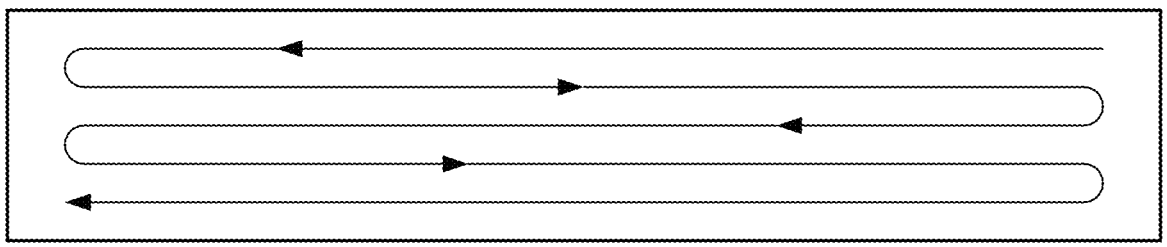
FIG. 6 is a block diagram of exemplary different scan patterns in accordance with one embodiment.
Figure 6:
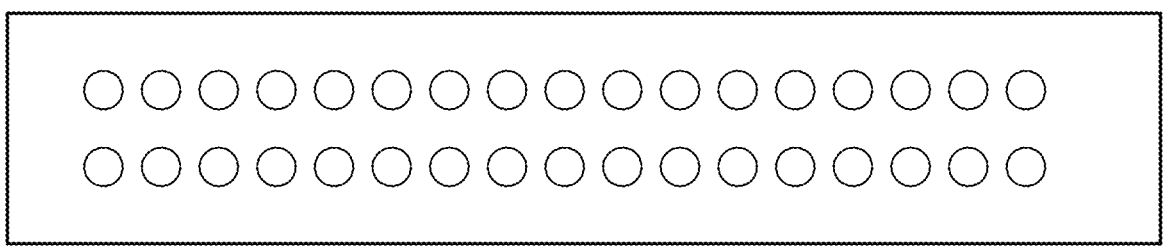
Figure 6:
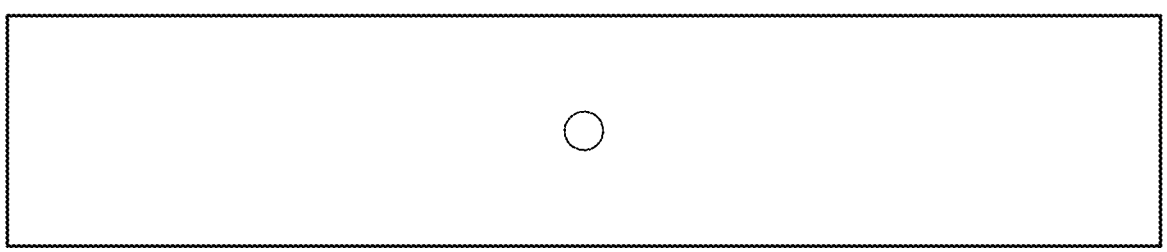

FIG. 6 is a block diagram of exemplary different scan patterns in accordance with one embodiment. The different scan patterns can include a raster scan approach, a spot scanning pencil beam approach, and/or a single pencil beam approach. Scanning magnets that are changed at 1-2500 Hz with raster or spot scanning can selectively irradiate targeted tissues and/or avoid healthy tissues.

In accordance with embodiments of the present invention, a combination of scanning and rapid changes in beam intensity may add more degrees of freedom to paint different layers of target tissue (e.g., tumors, etc.) in a third dimension, e.g., depth, when used in conjunction with particle beam entry angle control features (e.g., magnets, etc.) that adjust the beam (e.g., to be divergent, normal, convergent, etc.).

Some beam generation systems, for example, linear accelerators, e.g., LINAC 212 (FIG. 2A), may change beam energies at rates comparable to scanning rates, e.g., up to about 1000 times per second. It is appreciated that scanning and beam energy changes may take place at the same rate, in some embodiments. When coupled with a beam transport system, e.g., bend magnets 215, X, Y direction scan magnets 221 and/or 222 (FIG. 2A), that can accept a large range of beam momentums, many scanned beams may be at different energy levels. For example, a first spot beam may irradiate a volume at a first, relatively low beam energy, while a second spot beam may irradiate another volume at a second, relatively high beam energy. It is appreciated that beam energy is correlated with radiation depth. By a combination of scanning and changing beam energies at rapid rates, a patient may be irradiated at different depths with fine resolution in up to three dimensions, without rotation of a radiation source. In some embodiments the beam energy may be changed as the radiation source, i.e. the gantry, is rotated.

In accordance with embodiments of the present invention, a beam transport system may utilize a non-scaling fixed field alternating gradient (nsFFAG) magnet system to accept and/or direct particle beams having a wide range of momentums.

The use of a scanning beam with a transport system that has a larger momentum acceptance can also permit gantry motion as well. This allows a larger energy variation in the beam energy being delivered. In one embodiment, the larger momentum acceptance results in a broader range of kinetic energies that can be transported without a need for large changes in the beam optics, which in turn can enhance the beam depth delta. In one exemplary implementation, the path length to the tumor is not constant as the gantry rotates around the patient. The rotation can provide increased performance (e.g., better treatments/conformality, increased healthy tissue sparing, etc.) due to more solid angle coverage. The better angle coverage can enable utilization of more beam entry points to cover the tissue target volume (e.g., tumor, etc.) while the resulting dose is delivered in a manner that spares Organs at Risk from significant adverse impact. In one embodiment, there is a switchyard magnet system that sends the beam to multiple scanning nozzles that are faster than traditional mechanical motion-based systems at covering multiple delivery orientations/angles.

FIG. 7 is a block diagram of exemplary method 700 in accordance with one embodiment.

In 710, a particle beam is generated. The particle beam can be an electron beam, proton beam, and so on.

In 720, the particle beam is directed in a scan pattern. The scan pattern can include a raster scan pattern, a spot scanning pencil beam pattern, a single pencil beam pattern, and so on.

In 730, the entry angle of the particle beam is controlled. In one embodiment, controlling the entry angle of the particle beam includes directing the particles in the particle beam into substantially parallel paths. In one embodiment, controlling the entry angle of the particle beam includes directing the particles in the particle beam into convergent paths. In one embodiment, controlling the entry angle of the particle beam includes directing the particles in the particle beam into divergent paths. The entry angle of the particle beam can be altered based upon a dose delivery characteristic (e.g., high dose, low dose, etc.). The entry angle of the particle beam can be altered based upon a depth penetration characteristic (shallow, deep, etc.).

In 740, the particle beam is forwarded towards a target tissue.

Figure 8:
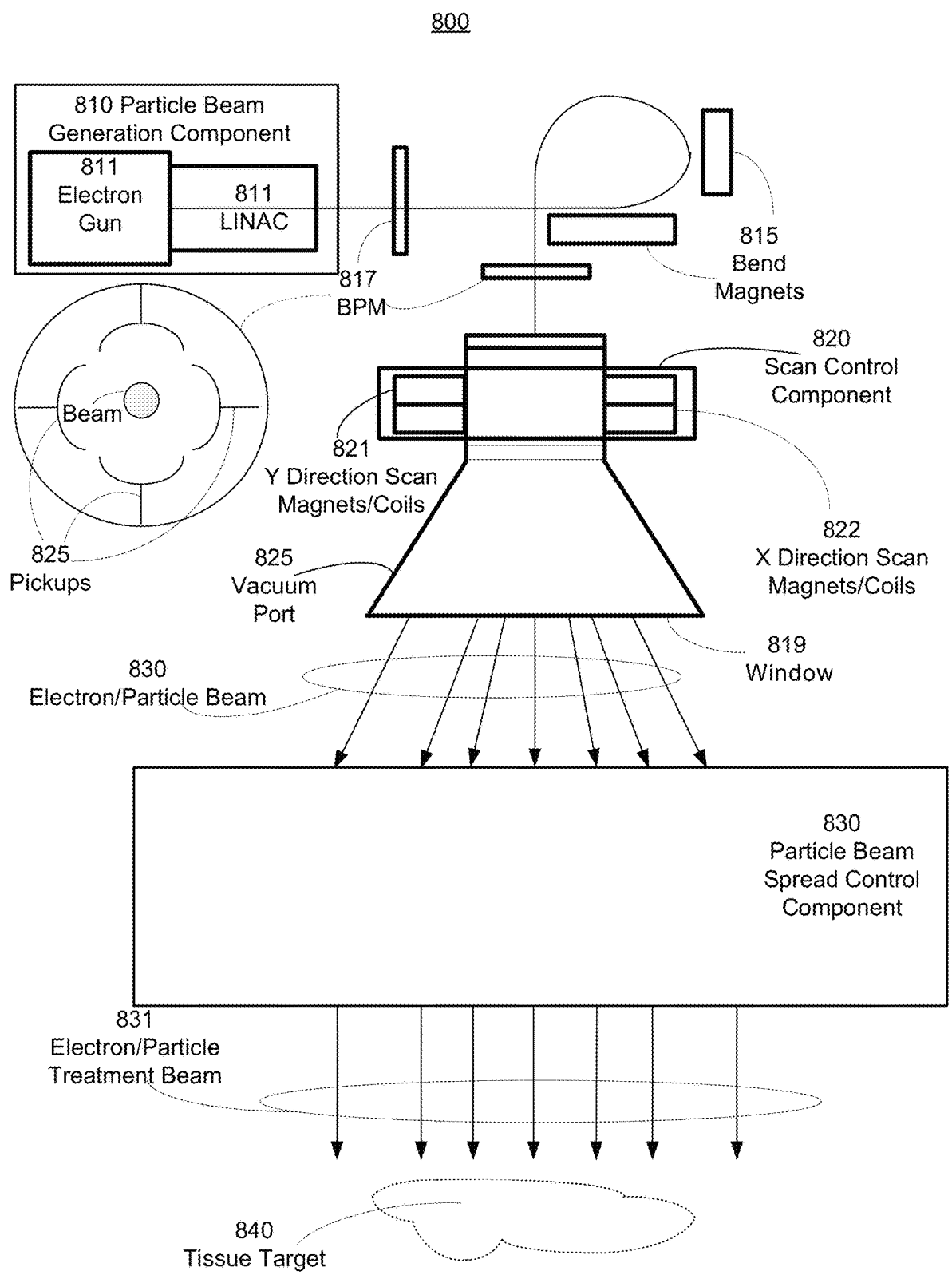
FIG. 8 is a block diagram of an exemplary system in accordance with one embodiment.

FIG. 8 is a block diagram of exemplary system 800 in accordance with one embodiment. System 800 includes particle beam generation component 810, bend magnets 815, beam profile monitor (BPM) 817, scan control component 820, vacuum port 825, window 819, and particle beam entry angle component 830. Particle beam generation component 810 generates a particle beam. In one embodiment, particle beam generation component 810 includes electron gun 811 and LINAC 812. The bend magnets 815 bend the particle beam directing the particle beam into the path of the scan control component 820, which directs the particle beam in a scan pattern. In one embodiment, scan control component 820 includes Y-direction scan magnets 821 and X-direction scan magnets 822. The particle beam flows from the scan magnets though the scan port 825 and window 819 towards the particle beam entry angle control component 830. The particle beam entry angle control component 830 adjusts the paths of the particles (e.g., electron paths, proton paths, etc.) and resulting entry angle of the electron treatment beam 831. Electron treatment beam 831 is directed towards tissue target 840.

Beam profile monitor (BPM) 817 monitors the particle beam path through system 800 and helps to keep the particle beam appropriately aligned with the magnets that are in the system. The BPM 817 can provide feedback for automated adjustment of components in system 800. In one exemplary implementation the feedback is provided to a computer system directing the control of components in system 800. In one embodiment, the Beam profile monitor (BPM) 817 includes pickups 825 that monitor the particle beam path.

It is appreciated that utilization of a beam profile monitor can enable various features. More of a system can be under vacuum because the number of windows (e.g., made from or that include various materials such as Beryllium (Be), Titanium (Ti), Kapton, etc.) can be reduced. There can be enhanced monitoring of particle beam response to scanning control (e.g., spot scan, raster scan, etc.). Multifunction magnets can be monitored after scanning, including dipole sector magnets used for parallel or normal incidence particle beam adjustment and focusing. In one embodiment, a beam profile monitor can facilitate implementation of various chamber features (e.g., multi-wire, extended ion chamber, segmented chamber, etc.).

In one embodiment, the particle beam scanning and entry angle adjustment control is utilized to avoid a proximate structure (e.g., healthy tissue, organ, etc.) while still shooting a distal structure (e.g., tissue target, tumor, etc.). The treatment beam can be scanned "around" the proximate structure. In one exemplary implementation, as the particle treatment beam would otherwise be moving over the region with the "proximate" structure, the particle generation component can be gated/turned off. The particle generation component can be gated/turned back on when the treatment beam is back over a desired treatment area. In one embodiment, a system can apply the particle treatment beam at different entry angle to help avoid the proximate structure. It is appreciated, various aspects of a system can contribute to adjusting the particle treatment beam entry angles. In one embodiment, adjusting a particle treatment beam entry angle (e.g., diverging, converging, etc.) can contribute to determination of an entry angle. In one exemplary implementation, adjusting system components (e.g., rotating a gantry, etc.) can contribute to determination of a particle treatment beam entry angle.

Thus, the delivery of particle beams (e.g., electron beams, proton beams, etc.) can be done by using scanning magnets and other magnetic elements to shape and modify particle beam distribution or spread. In one embodiment, the distribution or entry angle can be made flat (e.g., similar in multiple regions, etc.) or skewed (e.g., higher in a region of a 2D projection with respect to another region, etc.). The particles can be made divergent, convergent, or normally incident on the outer surface (e.g., skin, etc.) of a patient's body. In one embodiment, additional degrees of freedom are created in terms of the depth dose distributions. In one exemplary implementation, a convergent particle beam has a deeper dose distribution at a given energy than a normally incident particle beam, and a divergent particle beam has a shallower dose distribution at a given energy than a normally incident particle beam. The use of scanning and particle beam distribution or entry angle adjustment and control facilitate protection of tissue close to the outer surface layers of a patient (e.g., skin, etc.) and reduce the potential of detrimental side effects. In one exemplary implementation, scanning and particle beam distribution or entry angle adjustment spare the outer surface layers of detrimental side effects. In one embodiment, the presented systems align well with and support FLASH radiation therapy (RT) applications involving dose rates of greater than or equal to 40 grays per second (Gy/s) with a total faction delivered in the range of 10-30 GY to a tissue target (e.g., tumor site, etc.).

Figure 9:
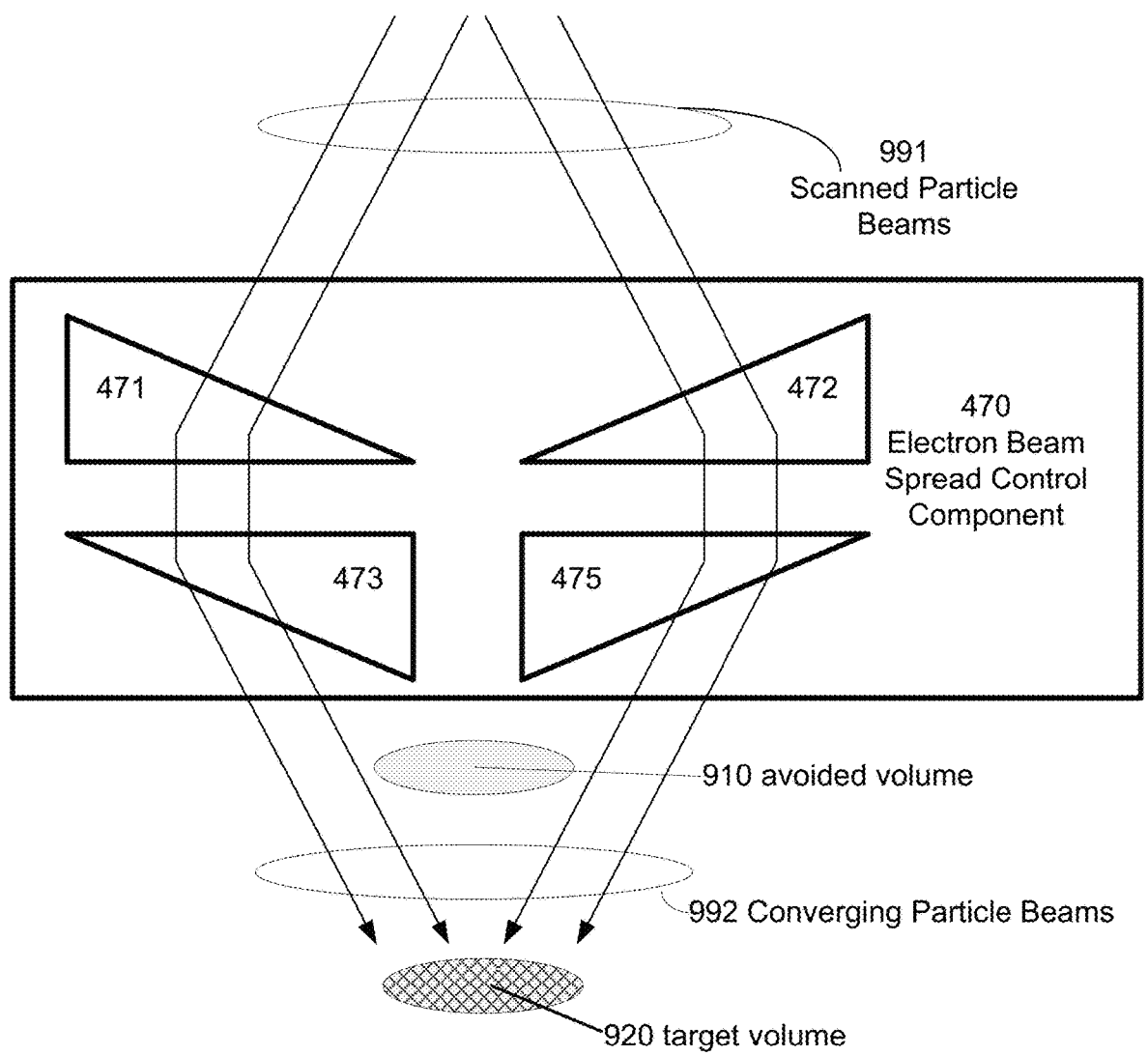
FIG. 9 illustrates a converging electron beam entry angle control arrangement for avoiding a volume at a first depth while delivering radiation to a volume at a greater depth, in accordance with embodiments of the present invention.

FIG. 9 illustrates a converging electron beam entry angle control arrangement 900 for avoiding a volume at a first depth while delivering radiation to a volume at a greater depth, in accordance with embodiments of the present invention. A divergent plurality of scanned particle beams 991 is generated and scanned, for example, as previously described with respect to FIG. 4C. The momentum of the plurality of particle beams 991 may also be changed, for example, as previously described with respect to FIG. 6, in some embodiments. The plurality of particle beams 991 is redirected by electron beam entry angle control component 470 into a plurality of converging particle beams 992. The converging particle beams 992 avoid a volume 910, e.g., an organ at risk, and delivers radiation to a target volume 920, e.g., a tumor. In this novel manner, volumes and/or tissues at a first depth may be targeted, while avoiding volume(s) and/or tissue(s) at a second depth that is closer to a radiation source than the first depth. Such embodiments may beneficially reduce an amount of gantry, e.g., gantry 320 (FIG. 3), rotation required to deliver a desired radiation dose to a target volume, e.g., a tumor, while avoiding other volumes, e.g., healthy tissue(s).

While most of the description is explained with an emphasis on medical radiation therapy applications, it is appreciated the present systems and methods can be readily implemented and utilized in a variety of other applications. In one embodiment, the systems and methods are utilized for other types of RT treatments besides FLASH. The scanning and particle beam entry angle control can be utilized in conjunction with an X-ray target utilized in Bremsstrahlung creation of X-rays. In one embodiment, the described particle beam distribution and entry angle adjustment control can be utilized in industrial products/applications.

Some portions of the detailed descriptions are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. Portions of the detailed description that follows are presented and discussed in terms of methods. Although steps and sequencing thereof are disclosed in figures herein describing the operations of those methods, such steps and sequencing are examples only. Embodiments are well suited to performing various other steps or variations of the steps recited in the flowcharts of the figures herein, and in a sequence other than that depicted and described herein.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "generating," "representing," "applying," "indicating," "storing," "using," "adjusting," "including," "computing," "displaying," "associating," "rendering," "determining," or the like, refer to actions and processes of a computer system or similar electronic computing device or processor. The computer system or similar electronic computing device manipulates and transforms data represented as physical (electronic) quantities within the computer system memories, registers or other such information storage, transmission or display devices. Terms such as "dose" or "dose rate" or "fluence" generally refer to a dose value or dose rate value or fluence value, respectively; the use of such terms will be clear from the context of the surrounding discussion.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media.

Computer storage media includes volatile and nonvolatile, removable and non-removable media implemented in any method or technology for storage of information such as computer-readable instructions, data structures, program modules or other data. Communication media can embody computer-executable instructions, data structures, and program modules, and includes any information delivery media.

Although the subject matter has been described in language specific to structural features and methodological acts, it is to be understood that the subject matter defined in the appended claims is not necessarily limited to the specific features or acts described above. Rather, the specific features and acts described above are disclosed as example forms of implementing the claims.

The invention claimed is:
1. A system comprising:
an electron gun configured to generate electrons;
a linear accelerator configured to accelerate the electrons in an electron beam;
a bend magnet configured to bend a path of the electron beam;

a scan control component including a plurality of scan coils, the scan control component configured to receive the electron beam and control movement of the electron beam by outputting the electron beam in a scan pattern; and an electron beam entry angle control component downstream of the scan control component in a beam travel direction, the electron beam entry angle control component including a plurality of magnets, and the electron beam entry angle control component configured to receive the electron beam output from the scan control component and control an entry angle of the electron beam.

2. The system of claim 1, wherein the electron beam entry angle control component includes a normal incident control component configured to receive an electron beam with electrons traveling in a diverging direction and redirect the electrons into a direction orthogonal to an exit surface of the electron beam entry angle component.

3. The system of claim 1, wherein the electron beam entry angle control component includes a convergent control component configured to receive an electron beam with electrons traveling in a diverging direction and redirect the electrons into a convergent direction.

4. The system of claim 1, wherein the electron beam entry angle control component is configured to control aspects of radiation impacts on a patient due to penetration of the electron beam.

5. The system of claim 1, wherein the electron beam entry angle control component is configured to control penetration characteristics of the electron beam into a patient, the penetration characteristics including radiation dose delivery to a tissue target.

6. The system of claim 1, wherein the electron beam entry angle control component is configured to control penetration characteristics of the electron beam into a patient, the penetration characteristics including avoidance of detrimental radiation impacts on non-target areas within a patient.

7. The system of claim 1, wherein the plurality of magnets include electro-magnets configured to create a magnetic field that changes divergent paths of the electrons in the electron beam to substantially parallel paths.

8. The system of claim 1, wherein the plurality of magnets includes multipole magnets configured to create a magnetic field that changes divergent paths of the electrons in the electron beam to convergent paths.

9. The system of claim 1, wherein the plurality of magnets includes sector magnets configured to create a magnetic field that changes divergent paths of the electrons in the electron beam to paths with a different divergence.

10. A method comprising:
generating a particle beam;
inputting the particle beam to a scan control component, the scan control component including a plurality of scan coils;
directing, by the scan control component, the particle beam by outputting the particle beam in a scan pattern;
receiving, by a particle beam entry angle control component, the particle beam output from the scan control component, the particle beam entry angle control component being located downstream from the scan control component in a direction of travel of the particle beam and including a plurality of magnets;
controlling, by the particle beam entry angle control component, an entry angle distribution of the particle beam in the scan pattern; and
forwarding the particle beam towards a target tissue.

11. The method of claim 10, wherein the particle beam is an electron beam.

12. The method of claim 10, wherein the controlling the entry angle distribution of the particle beam includes directing the particles in the particle beam into paths that are parallel to one another.

13. The method of claim 10, wherein the controlling the entry angle distribution of the particle beam includes directing the particles in the particle beam into convergent paths.

14. The method of claim 10, wherein the controlling the entry angle distribution includes altering the entry angle distribution of the particle beam based upon a dose delivery characteristic.

15. The method of claim 10, wherein the controlling the entry angle distribution includes altering the entry angle distribution of the particle beam based upon a depth penetration characteristic.

16. A system comprising:
a particle beam generation component configured to generate a particle beam;
a scan control component including a plurality of scan coils, the scan control component configured to receive the particle beam and control movement of the particle beam by outputting the particle beam in a scan pattern; and
a particle beam entry angle control component downstream of the scan control component in a direction of travel of the particle beam, the particle beam entry angle control component including a plurality of magnets, and the particle beam entry angle control component configured to receive the particle beam output from the scan control component and control an entry angle of the particle beam, the controlling including controlling a size of a cross-sectional area of the particle beam at varying distances from the particle beam entry angle control component.

17. The system of claim 16, wherein the particle beam entry angle control component is configured to receive the particle beam with particles traveling in a diverging direction and redirect the particles into a different diverging direction.

18. The system of claim 16, wherein the particle beam entry angle control component is configured to receive the particle beam with particles traveling in a diverging direction and redirect the particles into paths that are parallel to one another.

19. The system of claim 16, wherein the particle beam entry angle control component is configured to receive the particle beam with electrons traveling in a diverging direction and redirect the particles into a convergent direction.

20. The system of claim 16, wherein the particle beam entry angle control component is configured to control penetration characteristics of the particle beam into a patient, the penetration characteristics including radiation dose delivery to a tissue target.

21. The system of claim 16, wherein the particle beam entry angle control component is configured to control penetration characteristics of the particle beam into a patient, the penetration characteristics including avoidance of detrimental radiation impacts on non-target areas within the patient.

22. The system of claim 16, wherein the scan control component and the particle beam entry angle control component are coordinated to control the size of the cross-sectional area of the particle beam.

23. The system of claim 16, wherein the particle beam entry angle control component is configured to control a cross-sectional area of a raster or spot scanned pattern.

* * * * *